(12) United States Patent
Schabacker

(10) Patent No.: US 7,799,570 B2
(45) Date of Patent: Sep. 21, 2010

(54) METHODS FOR VALIDATING THE PRESENCE OF AND CHARACTERIZING PROTEINS DEPOSITED ONTO AN ARRAY

(75) Inventor: Daniel S. Schabacker, Naperville, IL (US)

(73) Assignee: Uchicago Argonne, LLC, Chicago, IL (US)

( * ) Notice: Subject to any disclaimer, the term of this patent is extended or adjusted under 35 U.S.C. 154(b) by 405 days.

(21) Appl. No.: 11/693,320

(22) Filed: Mar. 29, 2007

(65) Prior Publication Data

US 2008/0241965 A1 Oct. 2, 2008

(51) Int. Cl.
*G01N 33/00* (2006.01)
(52) U.S. Cl. .......................................... 436/86
(58) Field of Classification Search ........................ None
See application file for complete search history.

(56) References Cited

U.S. PATENT DOCUMENTS

2008/0241944 A1  10/2008  Schabacker

OTHER PUBLICATIONS

Schabacker et al. "Protein array staining methods for undefined protein content, manufacturing quality control, and performance validation", Anal. Biochem. 2006, 359:84-93.*
Martin et al. "Strategies and solid-phase formats for the analysis of protein and peptide phosphorylation employing a novel fluorescent phosphorylation sensor dye", Combinatorial Chemistry & High Throughput Screening, 2003, 6:331-339.*
Yan et al. "Protein microarrays using liquid phase fractionation of cell lysates", Proteomics, 2003, 3:1228-1235.*
Grubb et al. "Signal pathway profiling of prostate cancer using reverse phase protein arrays", Proteomics, 2003, 3:2142-2146.*
Schabacker et al., "Rapid Protein Array Fabrication Utilizing Host Derived Proteins," *Argonne National Laboratory*, (Abstract) (2006).
Schabacker et al., "Rapid Protein Array Fabrication Utilizing Host Derived Proteins," *BIO 2006 Innovation Corridor Poster Session*, Chicago, USA, (Poster) (2006).
Bruggemeier et al., "Use of protein-acrylamide copolymer hydrogels for measuring protein concentration and activity," *Analytical Biochemistry*, 329: 180-189 (2004).
Zhou et al., "Protein profiling by capillary isoelectric focusing reversed-phase liquid chromatography, and mass spectrometry," *Electrophoresis*, 26: 1381-1388 (2005).

\* cited by examiner

*Primary Examiner*—Karen Cochrane Carlson
*Assistant Examiner*—Bin Shen
(74) *Attorney, Agent, or Firm*—Barnes & Thornburg LLP; Alice O. Martin

(57) ABSTRACT

A method of determining if proteins have been transferred from liquid-phase protein fractions to an array comprising staining the array with a total protein stain and imaging the array, optionally comparing the staining with a standard curve generated by staining known amounts of a known protein on the same or a similar array; a method of characterizing proteins transferred from liquid-phase protein fractions to an array including staining the array with a post-translational modification-specific (PTM-specific) stain and imaging the array and, optionally, after staining the array with a PTM-specific stain and imaging the array, washing the array, restaining the array with a total protein stain, imaging the array, and comparing the imaging with the PTM-specific stain with the imaging with the total protein stain; stained arrays; and images of stained arrays.

7 Claims, No Drawings

METHODS FOR VALIDATING THE PRESENCE OF AND CHARACTERIZING PROTEINS DEPOSITED ONTO AN ARRAY

STATEMENT OF GOVERNMENT SUPPORT

This invention was partially conceived under Contract No. W-31-109-ENG-38 between the U.S. Department of Energy and the University of Chicago representing Argonne National Laboratory. Therefore, the Government has certain rights in the invention.

BACKGROUND

Methods and compositions are described of determining if proteins have been transferred to an array, and for characterization of the transferred (deposited) proteins.

The protein chip is a tool which is used in drug discovery and proteomics (i.e., the study of protein expression profiles and protein-protein interactions), not only for understanding basic cellular processes at the protein level, but also as a platform for next generation clinical and medical diagnostic devices or systems. Continued advances in protein chip technology, however, have been hindered by the very nature of proteins themselves. Variations in molecular weight, hydrophobicity, charge, stability, post-translational modifications (PTM), and accessibility of reactive side chains for immobilization are a few examples of protein heterogeneity that directly affect microarray fabrication, reproducibility, and multiplexed analyses. Variations in liquid handling, protein aggregation, buffer ionic strength, and sample viscosity likewise lead to significant variations in protein array manufacture and quality, necessitating the development of thorough quality assurance and quality control (QA/QC) methods for routine manufacturing practice.

As with nucleic acid arrays, dye incorporation can be used to confirm volume transfer from a printing system to a microarray substrate, but dye incorporation does not quantify the amount of protein transferred and functionally immobilized on the array. Likewise, a single, labeled, and co-deposited protein (analogous to an internally-doped oligonucleotide probe) may be a poor proxy for deposition/immobilization efficiency for proteins of substantively different physicochemical properties. While direct labeling of capture probes prior to deposition is possible for nucleic acids because hybridization is largely unaffected by 3' or 5' terminal fluors, equivalent protein labeling procedures may not only affect the physicochemical properties of the protein, but also consume reactive side chains necessary for the covalent immobilization process.

Creating functional protein arrays typically requires a sequenced genome, a well-characterized protein expression system, and labor-intensive expression and purification methods. In addition, the majority of proteins expressed in vitro lack PTMs that may be required for proper function or interaction, and expression systems for outer membrane proteins are still in their infancy. Practical difficulties associated with protein expression and purification are, therefore, obvious impediments to protein array manufacture and use, resulting in a number of new methods for generating protein array content.

A recently described two-dimensional liquid phase separation technique (PF2D) creates protein expression profiling maps. The PF2D fractions may create comprehensive, proteome-scale, functional protein arrays. Because proteins are generated in vivo by the organism of interest, a sequenced genome is not required in order to generate protein content reproducibly, and the resulting fractionated proteins retain all PTMs intact. Due to the uncharacterized nature of PF2D protein fractions, however, methods for confirming the successful transfer and abundance of uncharacterized PF2D fractionated proteins within microarray features becomes critical for subsequent assay development and interaction assay data interpretation.

SUMMARY

A method of determining if proteins have been transferred from liquid-phase protein fractions to an array is described. The method includes staining the array with a total protein stain and imaging the array with an array imager, whereupon staining is indicative of the transfer of protein to the array. The method can further include comparing the staining with a standard curve generated by staining known amounts of a known protein on the same or a similar array, whereupon the relative amount of proteins transferred from the liquid-phase protein fractions to the array is determined. Proteins do not need to be labeled prior to deposition on an array, therefore, identity of proteins in samples is not necessary prior to forming an array.

A method of characterizing proteins transferred from liquid-phase protein fractions to an array is also described. The method includes staining the array with a PTM-specific stain, such as a transmembrane stain, a glycoprotein stain, or a phosphoprotein stain, and imaging the array with an array imager. Staining of the proteins with the transmembrane stain indicates that transmembrane proteins were transferred, whereas staining of the proteins with the glycoprotein stain indicates that glycoproteins were transferred, and staining of the proteins with the phosphoprotein stain indicates that phosphoproteins were transferred. After staining the array with a PTM-specific stain and imaging the array with an array imager, the method optionally further includes washing the array, re-staining the array with a total protein stain, imaging the array with an array imager, and comparing the imaging with the phosphoprotein stain with the imaging with the total protein stain, whereupon, in the absence of positive PTM-specific staining, the presence of protein is determined, and, in the presence of positive PTM-specific staining, the amount of total protein that is post-translationally modified is determined.

In view of the above, a protein array, which has been stained with a total protein stain or a PTM-specific stain is provided. Also provided, is an image of a stained protein array, wherein the image is obtained with an array imager illuminated with an excitation wavelength of light appropriate for the stain.

The methods and compositions disclosed herein are suitable for use on arrays of small amounts of materials in the array elements. Array elements include gel drops and gel pads. Methods and composition are operative to detect proteins at a concentration of less than 1 ng/gel drop, even into the picogram level. Gel drops are used to form biochips.

Target proteins have been characterized, e.g., anti-ovalbumin and anti-ovalbumin serum albumin antibodies were deposited and immobilized onto gel element arrays. The arrays were used in an interaction assay to interrogate solutions containing various concentrations of the target proteins.

There was excellent correlation between signal intensity and amount of the phosphorylated protein, using a stain specific for phosphorylated proteins.

DETAILED DESCRIPTION

A relatively simple and straightforward method for assessing the quality (i.e., the presence of proteins) and character (i.e., PTM of proteins) of protein arrays (e.g., micro-arrays) fabricated from protein fractions, such as undefined protein fractions, e.g., those obtained from liquid-phase separation of proteins from whole cell lysates (e.g., PF2D fractions), is presented. Such a method facilitates understanding slide-to-slide variability and interpolating resulting signal intensity values after an interaction assay. By providing such a method, a significant step is made towards routine fabrication of whole-proteome arrays and the global analysis of functional protein:protein interactions, independent of sequenced genomes, affinity tags, and knowledge of target cell composition.

The liquid-phase protein fractions can be obtained in accordance with any suitable method known to those of skill in the art. For example, the fractions can be obtained from whole-cell lysates using PF2D, such as in accordance with the PROTEOSEP™ method of Eprogen, Inc. (Darien, Ill.).

The methods can be used with any protein array or micro-array. Preferably, the micro-array is a gel element protein array, which is conducive to preserving the functional integrity of immobilized proteins, including enzymes and antibodies.

Several simple total- and PTM-specific, on-chip staining methods are used to assess the quality (i.e., the presence of proteins) and character (i.e., PTM modifications of proteins) of protein arrays. The methods allow qualitative and relative quantitative assessment of the arrays prior to their use, such as in an on-chip interaction assay, and the obtainment of PTM information from interacting partners. The methods obviate the need to modify or label proteins prior to array deposition. The stains and arrays, however, should be protected from light.

The method of determining if proteins have been transferred from liquid-phase protein fractions to an array includes staining the array with a total protein stain and imaging the array with an array imager. Multiple arrays can be stained for purposes of quality control in batch productions. Staining is indicative of the transfer of protein to the array. One of ordinary skill in the art will readily appreciate that staining can involve pre-incubation, pre-washes, and/or post-washes depending on the particular stain used as exemplified herein in the "EXAMPLES." The method further includes comparing the staining with a standard curve generated by staining known amounts of a known protein on the same or a like array. The relative amounts of proteins transferred from the liquid-phase protein fractions to the array then can be determined.

Any suitable total protein stain can be used. The stain can be reversible or irreversible. Currently available irreversible stains have been found to be more sensitive than reversible stains. An example of a preferred total protein stain is DEEP PURPLE™ total protein stain (reactive component is epicoconone), which is available from Amersham Biosciences (Piscataway, N.J.) as RPN 6305. Other examples of fluorescent total protein stains include LAVAPURPLE™ (Fluorotechnics, Guelph, Ontario, Canada), Flamingo fluorescent gel stain (Bio-Rad Laboratories, Hercules, Calif.), SYPRO® Ruby (Invitrogen, Carlsbad, Calif.), and Krypton (Pierce Biotechnology, Rockford, Ill.).

A method of characterizing proteins transferred from liquid-phase protein fractions to an array is described. The method includes staining the array with a PTM-specific stain, such as a transmembrane stain, a glycoprotein stain, or a phosphoprotein stain and imaging the array with an array imager. Multiple arrays can be stained for purposes of quality control in batch production. Staining of the proteins with the transmembrane stain indicates that transmembrane proteins were transferred, whereas staining of the proteins with the glycoprotein stain indicates that glycoproteins were transferred, and staining of the proteins with the phosphoprotein stain indicates that phosphoproteins were transferred. One of ordinary skill in the art will appreciate that staining can involve pre-incubation, pre-washes, and/or post-washes depending on the particular stain used as exemplified herein. After staining the array with a PTM-specific stain and imaging the array with an array imager, the method can further include washing the array, re-staining the array with a total protein stain, imaging the array with an array imager, and comparing the imaging with the PTM-specific stain with the imaging with the total protein stain. In the absence of positive PTM-specific staining, the presence of protein is determined. In the presence of positive PTM-specific staining, the amount of total protein that is post-translationally modified is determined. For ratiometric analysis (e.g., determination of the amount of total protein that is post-translationally modified), it is preferred that the wavelength of light required for imaging with one stain does not overlap the wavelength of light required for imaging with the other stain.

Any suitable transmembrane stain can be used. While the stain can be reversible or irreversible, an irreversible stain has shown better results. An example of a transmembrane stain is PRO-Q® AMBER, which is available from Molecular Probes (Eugene, Oreg.) as M33308. Fluorescently tagged antibodies, which are specific for PTMs, including transmembrane domains, are commercially available.

Any suitable glycoprotein stain also can be used. While the stain can be reversible or irreversible, an irreversible has shown better results. An example of a glycoprotein stain is PRO-Q® EMERALD 488, which is available from Molecular Probes as P21875. Another example is Krypton glycoprotein stain (Pierce Biotechnology).

Any suitable phosphoprotein stain can be used. An irreversible stain has shown better results than a reversible stain. An example of a phosphoprotein stain is, PRO-Q® DIAMOND, which is available from Molecular Probes as P33301. Another example is PHOS-TAG™ 540 phosphoprotein stain (Perkin Elmer, Waltham, Mass.).

Any suitable array imager known in the art can be used in the above methods. Portable imagers are commercially available (see, e.g. Aurora Photonics, Inc., Lake Barrington, Ill.).

Similarly, any suitable array can be used in the above methods. The gel element array has several attributes that are conducive to PF2D array fabrication and the staining protocols utilized herein. For example, arrays developed with Pro-Q stains were successfully washed and re-stained with DEEP PURPLE™, providing a first approximation of PTM per unit of total protein immobilized on-chip. Successive deposition of protein (i.e., PF2D fractions) resulted in a linear increase in total immobilized protein per gel element; identical experiments with 2-dimensional substrates showed similar limits of detection (8-200 pg per spot at 2 SD over background), but uncorrelated and non-linear responses with increasing protein concentration per spot. The ability to re-load a gel element and achieve a linear increase in immobilized protein, in particular, provides a mechanism for further concentrating proteins on-chip prior to staining or interaction assays and militating against relatively low analytical sensitivity of the reporter (e.g., PRO-Q® AMBER) or analytical procedure (i.e., an interaction assay or low-affinity interacting partners). Preparative scale columns can be used to increase the amount of fractionated proteins for an array. The gel elements generated linear standard curves in both DEEP PURPLE™ and PRO® Q stains over at least 3-logs of deposited and immobilized protein, with the potential to increase the linear dynamic range through the use of more sensitive dyes/reporters (lower limit of detection) or repeated protein deposition per gel element (upper limit of detection). Finally, experiments with surface-biotinylated *Y. pestis* fractions indicate that native transmembrane proteins and PTMs survive both PF2D fractionation and gel element array manufacturing procedures, providing a basis for a genome-independent approach to study host-pathogen interactions at the whole-proteome level.

In view of the above, also provided is a protein array, which has been stained with a total protein stain or a PTM-specific stain, for example. The PTM-specific stain can be a transmembrane stain, a glycoprotein stain, or a phosphoprotein stain, for example. The array can be any suitable array, such as a gel element protein array.

Also in view of the above, an image of a stained protein array is provided. The image is obtained with an array imager illuminated with an excitation wavelength of light appropriate for the stain. Examples of appropriate excitation wavelengths for certain stains are provided in the "EXAMPLES."

EXAMPLES

The following examples are illustrative, they are not intended to limit the scope of the invention in any way.

Example 1

Preparation of a Whole Cell Lysate for Fractionation

An attenuated strain of *Y. pestis* designated KIM D27 was obtained from the laboratory of Dr. Olaf Schneewind at the University of Chicago (Chicago, Ill.). *Y. pestis* KIM D27 lacks the 102 kb pgm locus containing the Ybt iron transport system resulting in a strain that is avirulent through peripheral routes of infection. Heart infusion broth (2 ml; HIB; Difco Laboratories, Detroit, Mich.) was inoculated by loop from a −80° C. 15% glycerol stock of *Y. pestis* KIM D27 and incubated overnight at 27° C. on a roller drum. Cell density was monitored with a Biocrom WPA CO8000 Cell Density Meter to ensure cells were in log phase before induction. Induction of surface virulence proteins (type III secretion apparatus) was accomplished by inoculating 4 ml of $Ca^{2+}$-deficient media (1:20, in TMH) from the HIB log-phase culture. The culture was allowed to incubate for 2 hr at 27° C., followed by a 4 hr incubation at 37° C., at which time the culture was harvested by low-speed centrifugation. Cells were washed three times with cold phosphate-buffered saline (PBS) prior to lysis.

Lysis buffer (6 M urea, 2 M thiourea, 10% glycerol, 50 mM Tris-HCl, 2% N-octylglucoside, 5 mM TCEP (Tris(2-carboxyethyl)phosphine hydrochloride), and 1 mM protease inhibitor; 2 ml) was added to a cell pellet (0.5 ml), vortexed aggressively, and allowed to incubate 30 min at room temperature (RT). Six freeze/thaw cycles consisting of 3 min in dry ice/acetone followed by thawing at 42° C. and vortexing were performed. The lysate was centrifuged at 8,000 g for 60 min, and the supernatant was decanted and stored at −80° C. until fractionation.

Example 2

Fractionation of the Whole Cell Lysate of Example 1

*Y. pestis* KIM D27 lysate was fractionated using PROTEOSEP™ (two-dimensional liquid-phase fractionation) in collaboration with Eprogen. A PD-10 column (Amersham Biosciences) was equilibrated with approximately 25 ml of CF start buffer (6 M urea, 0.1% n-octyl glucoside, 25 mM triethanolamine). The supernatant from the whole cell lysate was loaded onto the PD-10 column. The proteins were eluted from the PD-10 column using CF start buffer, collecting the first 3.5 ml fraction of the eluent. Three ml of the fraction were injected onto a high performance chromatofocusing (HPCF) column and analyzed according to the PROTEOSEP™ protocol. After isoelectric focusing, the resultant samples were applied to a nonporous, reverse-phase, high-performance, liquid chromatography column (NPS—RP-HPLC) for fractionation based on hydrophobicity. An automated fractionater deposited 500 µl per well in nine 96-well microtiter plates.

Example 3

Preparation of Gel Element Protein Arrays

Polyacrylamide-based gel pad arrays were manufactured essentially as described by Arenkov et al. (2000). The N-hydroxysuccinimide ester of N-methacryloyl-6-aminocaproic acid (NHS monomer) was incorporated into the pre-polymer solution, thereby enabling covalent attachment of protein probes through available primary amines. Briefly, final concentrations of 2.92% acrylamide, 0.14% bis, 0.86% $N,N^1$-(1,2-dihydroxethylene) bisacrylamide (DHEBA), 40% glycerol, and 0.06% NHS monomer were combined in 0.2 M phosphate, pH 6.8, filtered through a 0.2 µm filter, and degassed for 2 min. The pre-polymer solution was applied to a casting cassette consisting of a Bind-Silane (Amersham) derivatized slide and a photolithographic mask containing 100×100 micron features at 300 micron center-to-center distance in a 4×(13×13) grid (676 gel elements per array). The assembled cassette was then exposed to an Oriel columnated UV light source for 500 sec to photopolymerize the gel pads according to the feature density and spacing dictated by the photolithographic mask. After photopolymerization, the cassette was disassembled in a water bath, and the gel element array matrices were washed with fresh MILLI-Q® water to remove glycerol and un-polymerized polymer and allowed to air dry. The resulting gel array matrices can be stored for up to 6 months desiccated at RT. Prior to depositing probes onto array matrices using a custom non-contact robotic arrayer, the gel pad matrices were placed in freshly prepared 0.1 M sodium periodate solution, which partially splits the DHEBA crosslinking molecules by oxidation of their vicinal dihydroxy groups resulting in an increase in porosity, for 30 min. Gel pad matrices were then washed and subjected to Repel-Silane (Amersham) treatment for one min to prevent cross-contamination between gel pads during the robotic deposition process.

Several proteins of varying physicochemical properties (e.g., glycosylation, phosphorylation, and transmembrane domain) were chosen as controls for establishing on-chip staining and quantitation procedures. Specifically, BSA (Pierce #23209; MW 66.4 kD), ovalbumin (Sigma #A5503; MW 42.7 kD; glycosylated and phosphorylated), ribonuclease B (Sigma #R7884; MW 15.0 kD; glycosylated), soybean trypsin inhibitor (Sigma #T9003; MW 22.0 kD), avidin (Pierce #21121; MW 68.0 kD; glycosylated), phosvitin (Sigma #P1253; MW 35.0 kD; phosphorylated), bacteriorhodopsin (Fluka #11708; MW 26.0 kD; glycosylated and transmembrane), and bovine gamma globulin (Pierce #23212; MW 150 kD; glycosylated) were chosen. Streptavidin-Texas Red (SA/TR; #21624, Pierce Biotechnology, Inc., Rockford, Ill.) and streptavidin-phycoerythrin (SA/PE; #15-4301, Zymed Laboratories, S. San Francisco, Calif.) reporters were used as controls to ascertain array performance. Briefly, each reporter was diluted to 1 µg/ml in TBST (Tris-buffered saline with 0.05% Tween-20 detergent) with 1% bovine serum albumin (BSA) and incubated independently over the array for 90 min, washed with TBST, and imaged on Argonne's portable imager.

One nanoliter of each control protein (1.0 mg/ml in PBS, pH 7.4) was loaded onto gel elements via non-contact pin transfer utilizing Argonne's custom-built robotic arrayer, resulting in approximately 1.0 ng of protein transferred per gel pad. Each protein was arrayed in triplicate. $A_{260}$ traces from the PF2D separation were used to identify *Y. pestis* KIM D27 fractions containing the highest protein concentration, which were subsequently loaded at 1, 3 or 5 depositions per gel pad, corresponding to 1, 3 or 5 mL of PF2D purified material. After deposition, arrays were incubated in 70% humidity chambers overnight at 5° C. to attach proteins covalently to the polymer backbone through the NHS-ester on the polymer and primary amines on the proteins. Loaded arrays were then washed with Tris-buffered saline (TBS) containing 0.1% Tween-20 to block remaining reactive NHS-esters and remove any non-immobilized protein. Control protein arrays were stored desiccated at 5° C. for up to 4 wk until use, whereas *Y. pestis* PF2D arrays were used within 24 hr of manufacture.

Example 4

Staining of Undefined Protein Fractions on the Gel Element Protein Arrays

DEEP PURPLE™ (DP) total protein stain (RPN6305) was obtained in kit form from Amersham, while PRO-Q® AMBER transmembrane stain (M-33308), PRO-Q® EMERALD 488 glycoprotein stain (P-21875), and PRO-Q® DIAMOND phosphoprotein stain (P-33301) were obtained from Molecular Probes. The stains utilized are irreversible in nature and are not intended to dissociate after interacting with the arrayed proteins. Stained arrays are not generally reusable for subsequent immunoassays or other protein:protein interaction experiments. When used as part of a quality control procedure, then, several arrays from a lot are evaluated as a representative sample of the entire manufacturing lot. Reversible protein stains are commercially available, but were not utilized due to known sensitivity limitations relative to the absolute quantity of total protein immobilized in any one gel element. On-chip staining and washing procedures essentially followed the manufacturer's instructions, taking care to protect arrays and stains from light. In brief, arrays were developed in DP by first incubating in 0.1% sodium dodecyl sulfate (SDS) for 1 hr at RT, briefly rinsing with MILLI-Q® water, and incubating in 200 mM $Na_2CO_3$ for 30 min. Arrays were then rinsed with MILLI-Q® water, 35 μl of a 1:200 dilution of DP stain were added, and the arrays were incubated for 1 hr at RT. Arrays were washed three times for 10 min each in 7.5% acetic acid, briefly rinsed with MILLI-Q® water, allowed to air dry, and finally imaged on Argonne's charge-coupled device (CCD)-based portable imager at 532 $nm_{ex}$/605 $nm_{em}$.

PRO-Q® AMBER transmembrane protein staining was accomplished by applying 35 μl of PRO-Q® AMBER stain to the array at RT for 2 hr. Arrays were then washed two times with Destain solution (5% methanol, 5% acetic acid) for 5 min each, followed by three 30-min washes with MILLI-Q® water at RT. Arrays were briefly rinsed with MILLI-Q® water, allowed to dry, and finally imaged on Argonne's thermally controlled imager (TCI) multicolor (CCD)-based imager at 480 $nm_{ex}$/590 $nm_{em}$.

PRO-Q® EMERALD 488 glycoprotein staining first required that arrays be incubated in Wash solution (3% acetic acid) twice for 10-20 min each. Wash solution was then replaced with oxidizing solution, and the arrays were incubated for 20 min. Arrays were again incubated in Wash solution three times for 20 min each. Arrays were then stained with 35 μl PRO-Q® EMERALD stain (Molecular Probes) for 2 hr, washed three times for 15 min each in wash solution, briefly rinsed with MILLI-Q® water, allowed to dry, and imaged on Argonne's TCI multicolor CCD-based imager at 480 $nm_{ex}$/535 $nm_{em}$.

PRO-Q® DIAMOND phosphoprotein staining was accomplished by incubating arrays with 35 μl PRO-Q® DIAMOND stain for 60 min, destaining in three washes of 30 min each in Destain solution (50 mM sodium acetate, 20% acetonitrile), washing twice with MILLI-Q® water at RT for 5 min each, rinsing once more with MILLI-Q® water, air drying, and imaging on Argonne's CCD-based portable imager at 532 $nm_{ex}$/605 $nm_{em}$.

All data were acquired on one of two imagers designed and fabricated at Argonne National Laboratory. The portable imager utilizes a 12-bit CCD camera with a 605 nm filter. The excitation sources consist of two 5 mW lasers at 532 nm. The field of view is illuminated by focusing the lasers through the side of the microscope slide containing the array. This side illumination results in an evanescent wave through the slide providing extremely uniform illumination. Acquisition times varied from 10-60 sec. The TCI multicolor 12-bit CCD-based imager utilizes a 100 W white light as the excitation source in conjunction with appropriate excitation and emission filters. Both imagers have a minimum optical detection limit of 2.4×107 Cy3 dye molecules or 7.2×107 Cy5 dye molecules per gel element. Image analysis software developed at Argonne National Laboratory was used for all data acquired. The imager and analysis software may be purchased from Aurora Photonics (Barrington, Ill.). Fluorescent intensities of replicate gel elements were averaged and corrected for background (average of adjacent replicate gel elements devoid of any protein). All data were collected in arbitrary units as follows. A cell size of 17×17 pixels was employed taking the sum of all signals within the cell. The resulting response curve of 0-1,183,455 was calculated by 4095 arbitrary units (12-bit camera provides 0-4095) per pixel×289 pixels (17×17 pixels) =1,183,455.

In order to determine if DP was suitable for QA/QC analysis of protein arrays and on-chip protein quantitation, BSA (Pierce #23209) and biotinylated BSA (B-BSA, Pierce #29130) were diluted in PBS and immobilized (n=12, 3 replicate gel elements across 4 arrays) in a two-fold dilution series from 2-2,000 pg per gel element. In parallel, B-BSA was diluted in 2-fold dilutions (from 0.64-2,000 pg per gel element) into a background of non-biotinylated BSA to maintain an overall concentration of 2 mg/mL total protein and 2,000 pg per gel element. Standard curves for B-BSA and native BSA stained with DP or detected via SA/TR or SA/PE reporters were generated. BSA was reproducibly immobilized and stained within replicate gel elements across 4 arrays. DP staining for BSA was linearly correlated over 3 logs of immobilized protein with a conservative detection limit of 8 pg per gel element (at 3 standard deviations (SD) over the mean background), exceeding the DP limit of detection for 2-D polyacrylamide gels by >60 fold (reported as 500 pg per spot in the Amersham user manual). B-BSA diluted in a background of non-biotinylated BSA was detected over a similar linear dynamic range and at a 0.64 pg limit of detection (at 3 SD over the mean background) when detected with either SA/TR or SA/PE. Gel elements containing >1 ng immobilized protein resulted in a saturated signal (60 sec exposure time); no attempts were made to adjust exposure times or manufacturing practices to quantify single protein concentrations exceeding 1 ng per gel element.

Since DP total protein stain allows on-chip protein quantification, DP was evaluated against a panel of immobilized control proteins with varied physicochemical properties printed in 2-fold serial dilutions from 1 pg to 1,000 pg per gel element (n=4) to assess potential variations in staining efficiency. Based on the average signal from four arrays and three replicate drops per array, the linear dynamic range was at least 3 logs for all tested proteins, with a minimum detection limit (at 3 SD over background) of 8 pg. Phosvitin was the most poorly stained protein ($R^2$=0.7) with a slope <1, indicating that phosvitin was not immobilized with the same efficiency as the other proteins; that phosvitin was not as stable as the other proteins after deposition, crosslinking, and storage; that DP does not stain all proteins with equal efficiency; or a combination of these factors. That the DP stain performs predictably and reproducibly at picogram levels of immobilized protein is encouraging for semi-quantitative analysis of protein array data, including protein arrays fabricated from undefined content (i.e., PF2D fractions). On the other hand, the observation does have implications for developing standard curves for undefined protein content (e.g., PF2D fractions), in that on-chip protein quantitation (either before or after an interaction assay) is necessarily relative to an external standard rather than an absolute quantitation (even if that standard is resident in the same array).

There was a linear correlation between the loaded volumes of PF2D fractions and estimated protein abundance per gel element for all 88 fractions. An estimated maximum of 197 pg of total protein (with 5 depositions) were immobilized per gel element for each of the 88 selected PF2D fractions.

The successful isolation, separation and immobilization of *Yersinia* outer membrane proteins was confirmed by biotinylating *Y. pestis* surface proteins prior to lysis/fractionation, and detecting biotinylated proteins immobilized on-chip with SA/TR according to the procedure described herein. As such, the DP staining strategy provided essential quality control and assurance that uncharacterized protein from *Y. pestis* PF2D fractions (including outer membrane proteins) was successfully, reproducibly and quantitatively transferred to the gel element arrays.

Having established that DP can be used to quantify previously uncharacterized, immobilized proteins on a gel element array, several specific stains were evaluated for their ability to identify phosphorylation, glycosylation, and transmembrane regions in immobilized proteins, even though the manufacturers acknowledge that the sensitivity of the specific stains is much lower than a total protein stain, such as DP (sensitivities: DP=0.5 ng, PRO-Q® AMBER transmembrane stain=10 ng, PRO-Q® EMERALD glycoprotein stain 488=4 ng, and PRO-Q® DIAMOND phosphoprotein stain=1-16 ng). For these experiments, then, the specific stains and protocols were tested against 1 ng of immobilized control protein per gel element, without regard to on-chip analytical sensitivity. Control proteins (with known PTMs) were immobilized at 1 ng per gel element. Data were obtained for replicate arrays, with three replicate elements per array (n+9) and a 10-sec total exposure time. All control proteins generated detectable signal over background (average background=7750±556 arbitrary units; n=145 blank gel elements), but only ovalbumin and phosvitin (known phosphoproteins) showed appreciable signal and a positive linear correlation between signal intensity and protein concentration. The successful transfer and presence of all control proteins was confirmed by restaining the same arrays with DP, as described herein. Glycosylated proteins (bovine gamma globulin, ovalbumin, RNase B, avidin, and bacteriorhodopsin) generated greater signal intensity than non-glycosylated proteins, but PRO-Q® EMERALD resulted in detectable signal (over background) for all proteins regardless of their glycosylation state. PRO-Q® AMBER also cross-reacted with other control proteins on the array, but again generated the highest absolute (background-corrected) signal against a transmembrane protein (bacteriorhodopsin). PRO-Q® EMERALD resulted in the greatest absolute background signal for the stains tested here (average background=23684±1328 arbitrary units representing 2% of the total response scale of 0-1,183,455; 10 sec exposure; n=145). Both PRO-Q® EMERALD and PRO-Q® AMBER also showed considerable non-uniform signal in the glass substrate field between gel elements, including streaks, precipitates and various edge effects on discreet gel pads that were not observed with PRO-Q® DIAMOND or DP stains. Resulting microarray optical artifacts affect calculations of absolute signal intensity and cross-reactivity in the microarray format.

Example 5

Characterization of a Target Protein in a Protein Fraction

Anti-ovalbumin and anti-BSA antibodies were deposited and immobilized onto gel element arrays. The array was then used in a simple interaction assay to interrogate solutions containing various concentrations of ovalbumin (a phosphorylated protein) and BSA (an unphosphorylated protein). Reacted arrays were then stained with PRO-Q® DIAMOND specific for phosphorylated proteins. There was an excellent correlation (R2=0.9547) between signal intensity and the amount of ovalbumin present in the solution, while no signal was present for the BSA.

All references, including publications, patent applications, and patents, cited herein are hereby incorporated by reference to the extent that they relate to materials and methods described herein.

The use of the terms "a," "an," "the," and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate better the invention and does not pose a limitation on the scope of the invention unless otherwise claimed. No language in the specification should be construed as indicating any non-claimed element as essential to the practice of the invention.

PUBLICATIONS CITED

Publications cited are incorporated by reference to the extent they relate to materials or methods disclosed herein.

Angenendt et al., Toward optimized antibody microarrays: a comparison of current microarray support materials. Anal Biochem 309:253-260 (2002).

Arenkov et al., Protein microchips: use for immunoassay and enzymatic reactions. Anal Biochem 278:123-131 (2000).

Delehanty et al., Method for printing functional protein microarrays. Biotechniques 34:380-385 (2003).

Gavin et al., Analysis of protein interaction and function with a 3-dimensional MALDI-MS protein array. Biotechniques 39:99-107 (2005).

Lin, K. Methods of Microarray Data Analysis III. Kluwer Academic, New York (2003).

Lubman et al., Two-dimensional liquid separations-mass mapping of proteins from human cancer cell lysates. J Chromatogr B Analyt Technol Biomed Life Sci 782:183-196 (2002).

O'Neil et al., Profiling the progression of cancer: separation of microsomal proteins in MCF10 breast epithelial cell lines using nonporous chromatophoresis. Proteomics 3:1256-1269 (2003).

Predki, P. F. 2004. Functional protein microarrays: ripe for discovery. Curr Opin Chem Biol 8:8-13 (2004).

Templin et al., Protein microarray technology. Trends Biotechnol 20:160-166 (2002).

Van Le et al., Functional characterization of the bladder cancer marker, BLCA-4. Clin Cancer Res 10:1384-1391 (2004).

Wang et al., Quantitative quality control in microarray experiments and the application in data filtering, normalization and false positive rate prediction. Bioinformatics 19:1341-1347 (2003).

Yan et al., Protein microarrays using liquid phase fractionation of cell lysates. Proteomics 3:1228-1235 (2003).

Yan et al., A comparison of drug-treated and untreated HCT-116 human colon adenocarcinoma cells using a 2-D liquid separation mapping method based upon chromatofocusing PI fractionation. Anal Chem 75:2299-2308 (2003).

Zheng et al., Two-dimensional liquid chromatography protein expression mapping for differential proteomic analysis of normal and O157:H7 *Escherichia coli*. Biotechniques 35:1202-1212 (2003).

Zhu et al., Identification of low molecular weight proteins isolated by 2-D liquid separations. J Mass Spectrom 39:770-780 (2004).

What is claimed is:

1. A method of determining if proteins have been transferred from liquid-phase protein fractions to an array, the method comprising staining the array with a total protein stain and imaging the array with an array imager, wherein staining is indicative of the transfer of protein to the array, and wherein the liquid-phase protein fractions are obtained from a whole cell lysate using two-dimensional liquid-phase fractionation, and wherein the array is a gel element protein array.

2. The method of claim 1, which further comprises comparing the staining with a standard curve generated by staining known amounts of a known protein on the same or a like array, wherein the relative amount of proteins transferred from the liquid-phase protein fractions to the gel element protein array is determined.

3. The method of claim 1 further comprising staining an array made from the same liquid phase protein fractions as the array stained with the total protein stain, with a post translational modification-specific (PTM-specific) stain, and comparing the results.

4. The method of claim 1, wherein the staining for total proteins is linearly correlated over 3 logs of immobilized protein with a detection limit of 8 pg per gel element.

5. A method of characterizing proteins transferred from liquid-phase protein fractions to an array, the method comprising staining the array with a post-translational modification-specific (PTM-specific) stain and imaging the array with an array imager, wherein staining of the proteins with the PTM-specific stain indicates that post-translationally modified proteins were transferred, wherein the liquid-phase protein fractions are obtained from a whole cell lysate using two-dimensional liquid-phase fractionation and wherein the array is a gel element protein array.

6. The method of claim 5, wherein the PTM-specific stain is selected from the group consisting of a transmembrane stain, a glycoprotein stain, a phosphoprotein stain, and a combination thereof.

7. The method of claim 5, wherein, after staining the array with a PTM-specific stain and imaging the array with an array imager, the method further comprises washing the array, restaining the array with a total protein stain, imaging the array with an array imager, and comparing the imaging with the PTM-specific stain with the imaging with the total protein stain, whereupon, in the absence of positive PTM-staining, the presence of protein is determined, and, in the presence of positive PTM-staining, the amount of total protein that is post-translationally modified is determined.

* * * * *